United States Patent [19]
Aho

[11] 4,057,856
[45] Nov. 15, 1977

[54] FIXING ARRANGEMENT FOR THE SEALING PAD ON THE EAR HOOD OF A HEARING PROTECTION MEANS

[75] Inventor: Yrjö Aho, Westend, Finland

[73] Assignee: Exel Oy, Helsinki, Finland

[21] Appl. No.: 657,700

[22] Filed: Feb. 12, 1976

[30] Foreign Application Priority Data

Feb. 14, 1975    Finland .................................. 750412

[51] Int. Cl.² .......................................... A41D 21/00
[52] U.S. Cl. .................................................... 2/209
[58] Field of Search ...................... 2/209; 179/182 R; 181/20, 129

[56] References Cited

U.S. PATENT DOCUMENTS 3,073,410  1/1963  Gongoll et al. ........................ 2/209
3,408,658  11/1968  Beguin et al. ........................... 2/209

FOREIGN PATENT DOCUMENTS 606,405  10/1960  Canada .................................... 2/209
301,034  11/1915  Germany ......................... 179/182 R Primary Examiner—Werner H. Schroeder
Assistant Examiner—Peter Nerbun

[57] ABSTRACT

A hearing protection means having an ear hood and an annular washer plate releasably secured thereto with mating surfaces therebetween. An annular sealing pad is provided having an annular skirt portion which is adapted to be secured to the hearing protection means between the mating surfaces of the ear hood and annular washer plate.

3 Claims, 5 Drawing Figures

FIXING ARRANGEMENT FOR THE SEALING PAD ON THE EAR HOOD OF A HEARING PROTECTION MEANS

The present invention concerns a fixing arrangement for the sealing pad of a hearing protection means wherein the fixing is accomplished by using a skirt belonging to the sealing pad made of plastic foil, the circumference of the ear hood having a groove for said skirt.

The soft annular, cushion-like sealing pad interposed between the ear hood of the hearing protection means and the user's skin is almost without exception made of plastic foil of 0.2 to 0.4 mm thickness by joining separate pieces of same, and it is filled with foamed plastic or with a liquid.

In some instances the sealing pad is affixed to its base with cement, this base consisting of the annular base part of the ear hood, but it is more common in view of facilitating the replacement of a damaged or soiled sealing pad, to provide the sealing pad with an external skirt, which is stretched over the rim of the ear hood to keep the sealing pad in its place. In order to avoid the risk of detachment of the sealing pad, it is known in prior art through the teachings of the Finnish Pat. No. 46,023, to provide the circumference of the ear hood with a deep groove receiving the skirt. Hereby the risk of unintended detachment of the sealing pad has been successfully avoided, and at the same time its replacement has been made possible. But this arrangement of prior art has the drawback that the manufacturing of an ear hood having the said groove is cumbersome and requires expensive press tools, or alternatively the groove has to be produced by machining afterwards. It has also proved somewhat inconvenient to fit the skirt in the groove.

The object of the invention is to provide a combination arrangement of the type described having components which are easy to manufacture and easy to assemble and by the aid of which a positive and tight attachment of the sealing pad as well as easy replacement of the sealing pad are ensured.

This object is accomplished by the present invention mainly in that the arrangement comprises a separate annular sealing pad washer plate component, in which the annular sealing pad is supported on the annular washer plate mating surfaces having been provided on said washer plate and on the ear hood on their outer circumference, that on the outer rim of the bottom of the sealing pad there has been affixed an inwardly directed skirt consisting of plastic foil, and that when the ear hood has been assembled into condition ready for use the said skirt is impacted between the said mating surfaces.

It is found that with this arrangement the ear hood and the washer plate are both easily producible as plastic pressings and that it is easy work to fit the skirt of the sealing pad around the rim of the separate washer plate. When the washer plate is pressed to attach to the ear hood by snap action, the skirt of the sealing pad will be impacted between the mating surfaces of the hood and the washer plate, whereby positive attachment and sealing are obtained.

The invention is more closely described in the following with reference to the attached drawings, wherein:

FIG. 1 presents the ear hood in sectional view, and

Figure 1:
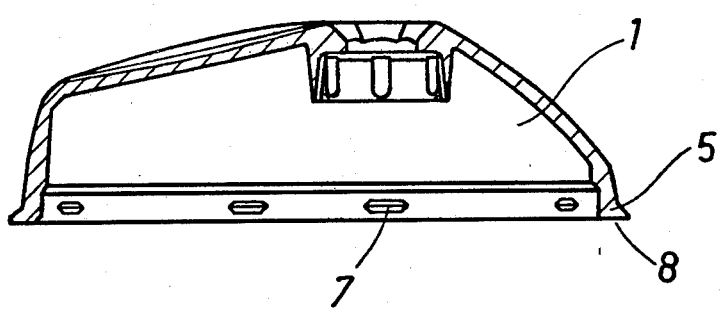
Figure 2:
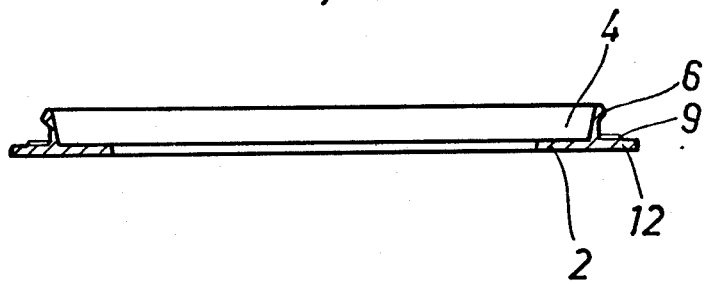
FIG. 2 shows the washer plate of the sealing pad, intended for attachment to the ear hood, in sectional view.
Figure 3:
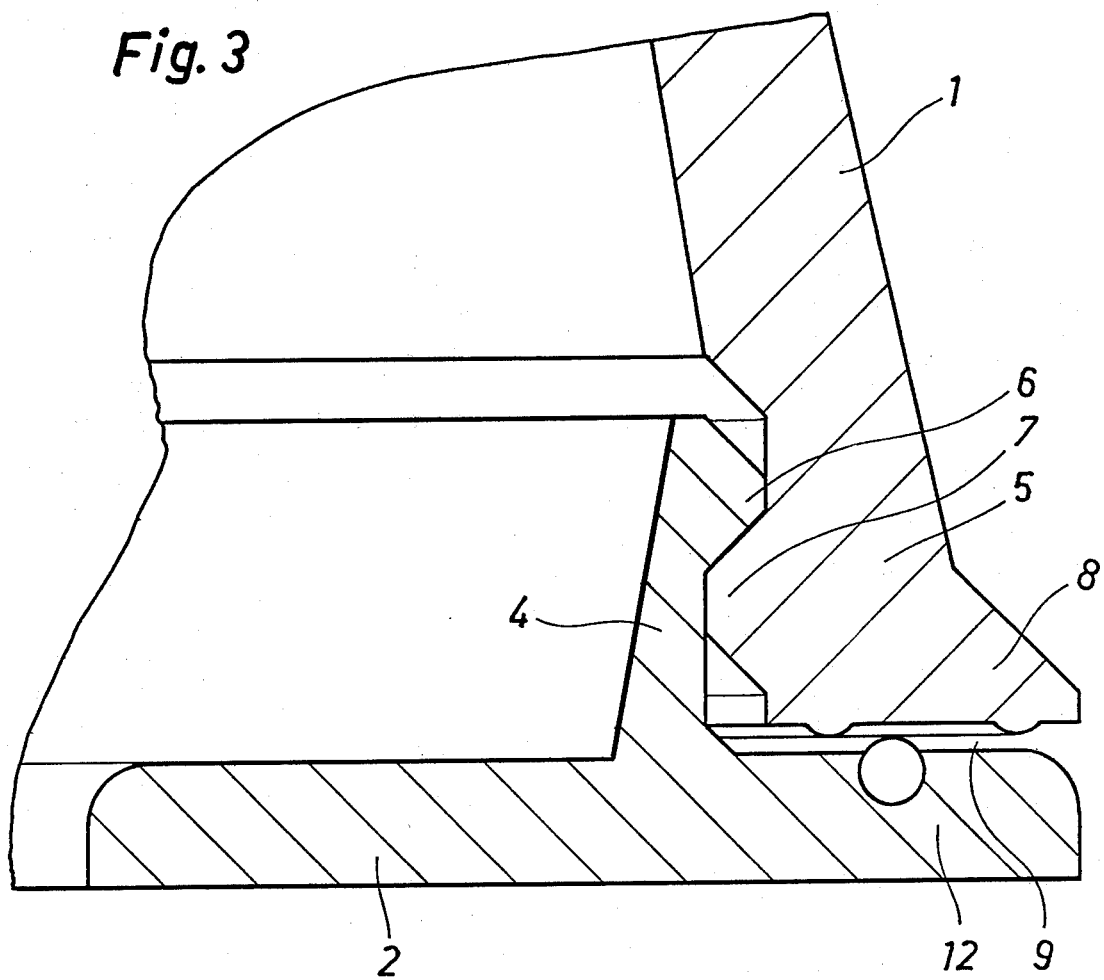
FIG. 3 shows, on a larger scale, a section through the marginal part of the joined ear hood and washer plate.

Referring to begin with, to FIGS. 1 to 3, the design of the ear hood and of the washer plate of the sealing pad and their mutual attachment shall now be described. For the attachment to each other of the washer plate 2 and the ear hood 1, there projects from the washer plate 2 a fixing flange 4, which can be pushed to reside within the rim 5 of the ear hood 1. The fixing flange 4 has on its outer rim an annular ridge 6, and the rim 5 of the ear hood has on its inner surface eminences 7, behind which the annular ridge 6 may be made to enter by snap action. When this is done, the marginal surface 8 of the ear hood and the mating surface 9 of the washer plate come to lie against each other as shown in FIG. 3.

Figure 4:
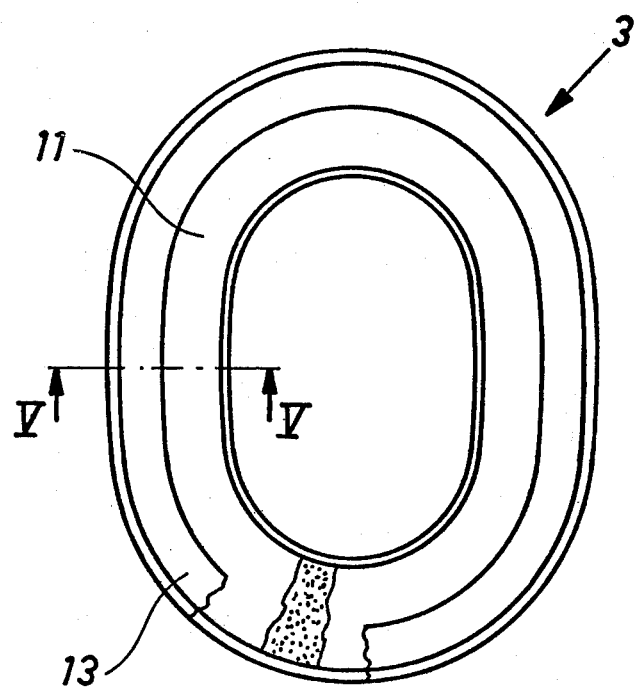
FIG. 4 shows the sealing pad, viewed from its underside.
Figure 5:
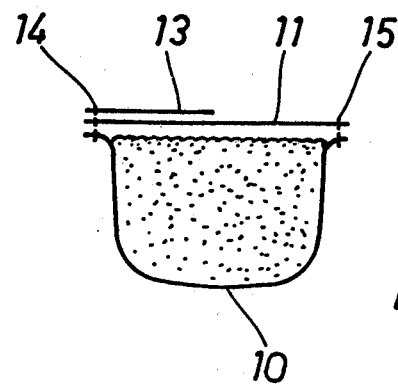
FIG. 5 shows the section carried along the line V—V in FIG. 4.

The sealing pad 3 shown in FIGS. 4 and 5 consists of the outer foil 10, the bottom foil 11, which comes to rest against the washer plate 2, and the skirt foil 13 meant to be placed over the rim 12. The space between the foils 10 and 11 contains a padding consisting e.g. of foamed plastic, and the foils have been joined at the edges by welded seams 14 and 15.

The skirt 13 consists of a soft, resilient material, for instance of the same material as the outer foil 10. It is then easily placeable around the rim 12 of the washer plate 2. When subsequently the washer plate 2 is affixed to the ear hood in the manner already described, the skirt 13 will be impacted between the mating surfaces 8 and 9. The mating surfaces 8 and 9 may additionally be provided with suitable annular eminences to enhance the sealing and attachment of the skirt.

I claim:

1. An arrangement for fixing a sealing pad to an ear hood of a hearing protection means, comprising an ear hood having an annular marginal surface, an annular washer plate member provided with an outer annular marginal surface for mating engagement with the annular marginal surface of the ear hood, said washer plate member and ear hood being releasably secured to each other and an annular sealing pad provided around its outer edge with an inwardly directed annular skirt portion, said skirt portion being gripped between the mating surfaces of said washer plate member and said ear hood when assembled, and said annular sealing pad being supported on said annular washer plate member.

2. An arrangement as claimed in claim 1 wherein the skirt of said sealing pad is composed of a soft plastic material and wherein said mating surfaces are each provided with annular ribs for enhancing attachment and sealing thereof between said surfaces when assembled.

3. An arrangement as claimed in claim 1 wherein said ear hood and said washer plate are provided with means inwardly of said mating surfaces thereof for providing a snap action therebetween when the arrangement is assembled.

* * * * *